Figure 1:
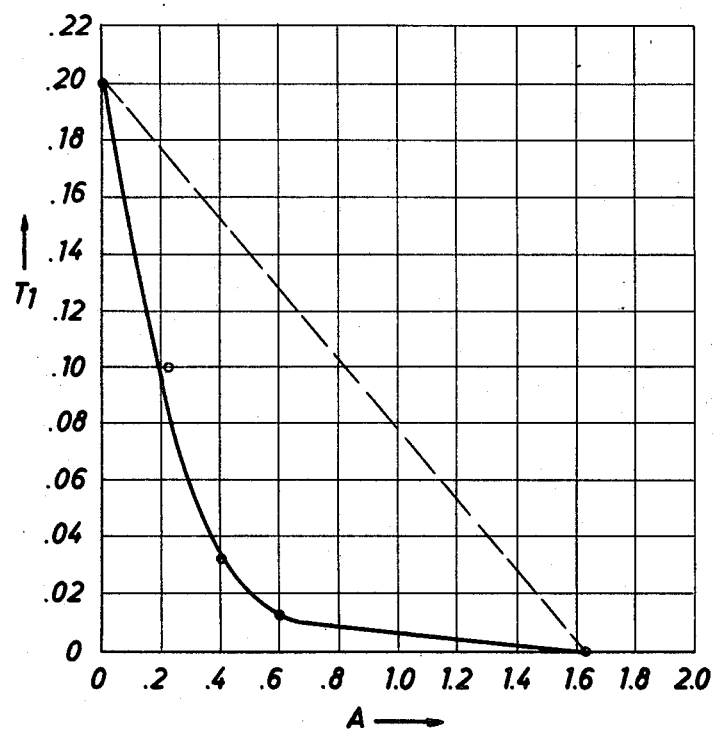

United States Patent [19]

Raven et al.

[11] 4,353,733

[45] Oct. 12, 1982

[54] HERBICIDE MIXTURE

[75] Inventors: Clive A. Raven; Alan J. Sampson, both of Sittingbourne, England

[73] Assignee: Shell Oil Company, Houston, Tex.

[21] Appl. No.: 28,766

[22] Filed: Apr. 10, 1979

Related U.S. Application Data

[62] Division of Ser. No. 902,124, May 2, 1978, abandoned.

[30] Foreign Application Priority Data

May 3, 1977 [GB] United Kingdom .............. 18435/77

[51] Int. Cl.³ ............................................ A01N 43/70
[52] U.S. Cl. .......................................... 71/93; 71/111
[58] Field of Search .................................... 71/93, 111

[56] References Cited

U.S. PATENT DOCUMENTS 3,505,325  4/1970  Schwarze .......................... 71/93 X
3,598,859  8/1971  Yates et al. ....................... 71/111 X

*Primary Examiner*—Catherine L. Mills

[57] ABSTRACT

Herbicidal compositions comprising an N,N-disubstituted alanine derivative and 2-ethylamino-4-(1-cyano-1-methyl ethylamino)-6-chloro-1,3,5-triazine or 2-ethylamino-4-(1-cyano-1-methyl ethylamino)-6-methylthio-1,3,5-triazine exhibit synergistic responses against wild oats. The addition of phenoxy-alkanoic acid derivatives, whether as racemate or R-(+)-isomers, causes an improved effect on yields without substantial loss of activity against wild oats.

6 Claims, 2 Drawing Figures

HERBICIDE MIXTURE

This application is a Division of Ser. No. 902,124, filed May 2, 1978, now abandoned.

The present invention relates to herbicidal compositions active against wild oats as well as to a method of controlling or eradicating wild oats in cereal crops by applying to a locus a herbicidally active composition according to the present invention.

Wild oat (*Avena fatua*) is a major world-wide weed problem and is becoming an increasing competitor to cereal grain crops. As a result the annual economic losses resulting from wild oat infestations are considerable.

An established family of compounds which has shown a very high level of activity towards wild oat and also a marked selectivity towards cereals comprises N,N-disubstituted-alanine derivatives, for example SUFFIX-herbicide for use in wheat and BARNON-herbicide for use in barley.

It has now been found that by mixing one of these N,N-disubstituted-alanine derivatives (as hereinafter defined) with BLADEX ® Herbicide (2-ethylamino-4-(1-cyano-1-methyl ethylamino)-6-chloro-1,3,5-triazine) or with 2-ethylamino-4-(1-cyano-1-methyl ethylamino)-6-methylthio-1,3,5-triazine and employing the mixture as a wild oat herbicide, synergistic responses are obtained.

It has further been found that the additional presence of certain phenoxy-alkanoic acid derivatives in the mixtures according to the present invention apart from their expected activity against broad-leaved weeds also gives rise to an increased activity of such tertiary mixtures on oats so that an improved yield can be obtained without or without substantial loss of activity against wild oats. In particular the presence of R-(+)-phenoxy-alkanoic acid derivatives leads to an improved performance.

Accordingly, the invention provides a herbicidal composition which contains as active ingredients at least:

(a) 2-ethylamino-4-(1-cyano-1-methyl ethylamino)-6-chloro-1,3,5-triazine or 2-ethylamino-4-(1-cyano-1-methyl ethylamino)-6-methylthio-1,3,5-triazine; and (b) an N,N-disubstituted alanine derivative having the following general formula:

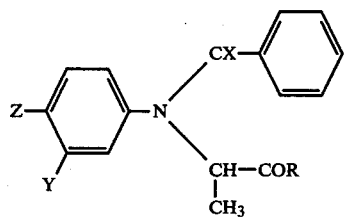

(I)

wherein Y and Z each individually represents a chlorine or fluorine atom; X represents an oxygen or sulphur atom; and R represents a group of formula —OR$_1$ in which R$_1$ represents a hydrogen atom, a metal salt-forming or an optionally alkyl substituted ammonium ion, or an optionally substituted alkyl, cycloalkyl, aryl, alkenyl or alkaryl group; a group of formula —SR$_2$ in which R$_2$ represents an optionally substituted alkyl, cycloalkyl, aryl, alkenyl or alkaryl group; or a group of formula —NR$_3$R$_4$ or —ON=CR$_3$R$_4$ in which R$_3$ and R$_4$ each individually represents a hydrogen atom, a hydroxy, an optionally substituted alkyl, alkenyl, aryl, alkaryl, heterocyclic, alkoxy, alkylthio or amino group, or R$_3$ and R$_4$ together represent a polymethylene group optionally interrupted by one or more hetero atoms.

The compositions according to the present invention may also contain a phenoxy-alkanoic acid derivative of the general formula:

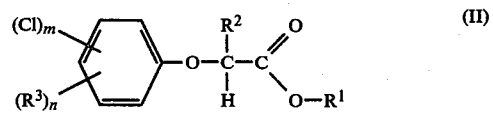

(II)

wherein R$^1$ represents an optionally substituted alkyl, cycloalkyl, alkenyl, aryl or aralkyl group; R$^2$ represents an alkyl group of up to 4 carbon atoms; R$^3$ represents an alkyl group of up to 4 carbon atoms; n is 0 or an integer up to 4 and m is 0 or an integer up to 5.

The optional substituents in the alanine derivative referred to above are preferably one or two chlorine or fluorine atoms, or alkyl or alkoxy groups with up to 4 carbon atoms. The alkyl, alkenyl, alkoxy and alkylthio groups referred to in the above general formula suitably contain up to 6 carbon atoms, preferably up to 4 carbon atoms. The aryl, alkaryl, cycloalkyl, heterocyclic and polymethylene groups referred to in the above general formula suitably contain up to 10 carbon atoms, preferably up to 7 carbon atoms. The hetero-atoms which may be present in the polymethylene group or in the heterocyclic group can be oxygen, nitrogen or sulphur atoms but are preferably one or two oxygen and/or nitrogen atoms.

When phenoxy-alkanoic acid derivatives are present in the compositions according to the present invention, preference is given to compounds according to formula II wherein R$^1$ represents an alkyl group of up to 18 carbon atoms; R$^2$ represents a methyl group; R$^3$ represents a methyl group; n is 0 or 1; and m is 1, 2 or 3. Particularly preferred are the long-chain alkyl esters of (4-chloro-2-methyl phenoxy)-propionic acid such as the esters of linevol (C$_7$–C$_{11}$ alkanol) and 2-ethyl hexanol.

The synergistic responses can be especially obtained using mixtures comprising either of the triazine compounds with a (3-chloro-4-fluorophenyl) alanine derivative, that is to say a compound according to the general formula I wherein Z is fluorine and Y is chlorine.

Examples of the N,N-disubstituted alanine derivatives referred to hereinabove and suitable methods of synthesis thereof can be found, for instance, in the following British patent specification Nos.: 1,164,160; 1,289,283; 1,413,286; and 1,437,711.

Especially preferred alanine derivatives to be used in the compositions according to the invention are those having the following general formula:

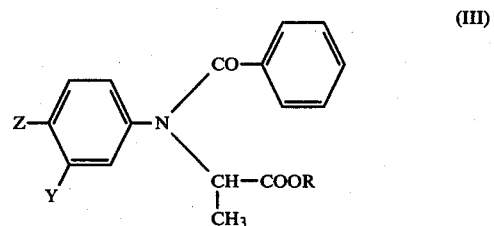

(III)

wherein Y represents a chlorine atom; Z represents a fluorine atom; and R represents a hydrogen atom or an alkyl group containing up to 6 carbon atoms, e.g. methyl, ethyl or isopropyl. Of these compounds one of the best to combat wild oat in barley crops is the compound having the formula III above wherein Y represents a chlorine atom; Z represents a fluorine atom; and R represents an isopropyl group. One of the best compounds for use in wheat crops has the formula III above wherein Y represents a chlorine atom; Z represents a fluorine atom, and R represents a methyl group.

The alanine derivatives according to formula I or III can exist in optically-active forms and, generally speaking, the laevo-rotatory isomer is the most active form and, thus, where it is appropriate, the alanine derivative may be employed in its most active optically-active form in compositions according to the invention.

The phenoxy-alkanoic acid derivatives according to formula II also exist in optically-active forms, and, generally speaking, the R-(+)-phenoxy-alkanoic acid derivatives are the most active. Where appropriate, the racemates as well as the R-(+)- isomers of the phenoxy-alkanoic acid derivatives according to formula II can be used in the mixtures comprising at least an N,N-disubstituted alanine derivative according to formula I and a triazine as specified hereinbefore.

Testing at a number of dosage levels indicates that compositions according to the invention exhibit a synergistic level of herbicidal activity with respect to wild oats. This means that considerably smaller amounts of the respective active ingredients can be used in the compositions than when applying each of them separately. The present invention makes it possible to control wild oat over a wide range of its development by post-emergence foliar application, whilst in the event that the mixtures also comprise a phenoxy-alkanoic acid derivative, broad-leaved weeds can be controlled as well.

It should be noted that although an increase in the effect of compositions upon cereal grains has been found to occur together with the marked increase in activity against wild oat, this effect does not seriously affect the cereal crop in practice since the amounts of alanine compounds required to cause a substantial increase are rather high.

Wild oat can be controlled in cereal crops by applying from 0.1 to 1.5 kg/ha of the compositions according to the present invention wherein the weight ratio of the alanine derivative to the triazine compound is in the range 50:1 to 1:1, preferably 20:1 to 5:1.

The amount of phenoxy-alkanoic acid derivative to be applied in mixtures containing an N,N-disubstituted alanine derivative according to formula I and a triazine as specified hereinbefore can be as high up as up to 8 kg/ha, preference being given to an amount in the range of from 1.5 to 4 kg/ha.

The herbicidal compositions according to the invention may also employ a carrier, a surface-active agent or both a carrier and a surface-active agent to facilitate application of the composition to wild oat infested land at the desired dosage rates. The term "carrier" as used herein means a solid or fluid material, which may be inorganic or organic and of synthetic or natural origin.

Typical solid carriers include natural and synthetic clays, natural silicates and aluminium silicates. Typical fluid carriers are ketones, aromatic hydrocarbons, petroleum fractions, and chlorinated hydrocarbons. Mixtures of liquids are often suitable.

One or more surface-active agents and/or stickers can be included in the formulations. The surface-active agent may be an emulsifying agent or a dispersing agent or a wetting agent; it may be non-ionic or ionic. Any of the surface-active agents usually applied in formulating herbicides or insecticides may be used.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The invention also includes a method of selectively controlling wild oat in cereal crops which comprises applying a composition according to the invention to a tract of land which is bearing cereal crops and infested with wild oat.

The compositions according to the present invention can be supplied to the wild oat plants in a conventional manner. The dust and liquid compositions may be conveniently applied by the use of power-dusters, boom and hand sprayers, and spraydusters. The compositions can also be applied from aeroplanes as a dust or spray because of the effectiveness of the compositions at low dosages.

The compositions according to the present invention may contain of from 0.5 to 75% by weight of active ingredients. The amounts to be applied will largely depend on the specific type of composition to be used and are well-known to those skilled in the art.

The invention is further illustrated by the following Examples in which to show the effect of the compositions according to the invention on wild oats (*Avena fatua*) in cereal crops, cultivated oats (*Avena sativa*) were used. It has been found from the Applicant's experience in this field that data obtained from tests on cultivated oats is entirely representative of the effect on wild oats and in many respects is more reliable in that the results are reproducible.

The synergistic responses obtained for mixtures comprising two active ingredients (i.e. an N,N-disubstituted alanine derivative and a triazine as specified hereinbefore) are best illustrated by means of diagrams. In the diagrams, given in the FIGS. 1–6, the horizontal axis indicates the amount of alanine compound in kg/ha (A) and the vertical axis indicates the amount of 1,3,5-triazine compound in kg/ha (T). The dotted line indicates the composition of any mixture calculated as showing an additive activity for a given growth reduction in the growth of weed or crop. This line can be found by connecting the amounts required for a given reduction in growth for each compound when applied alone.

Figure 2:
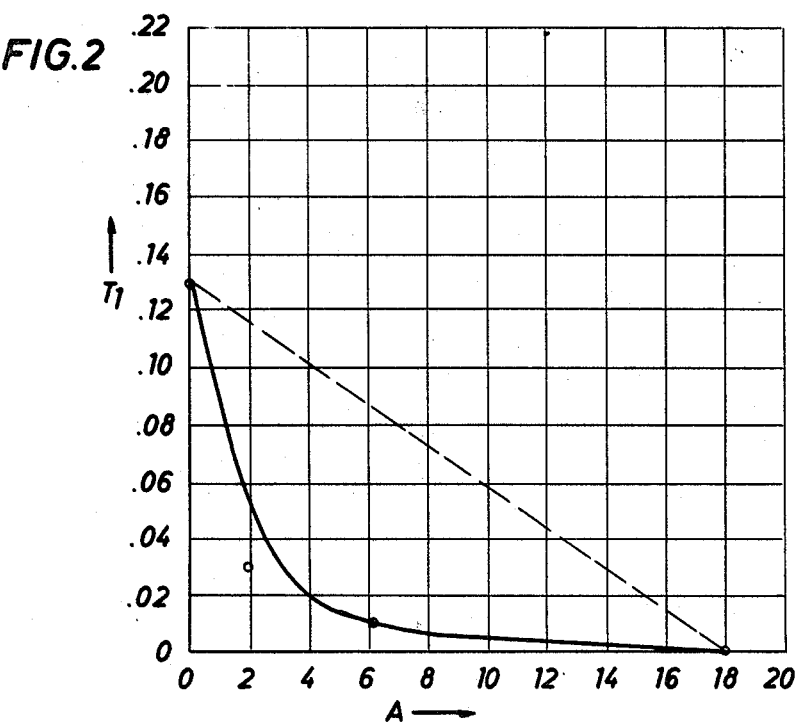
Figure 3:
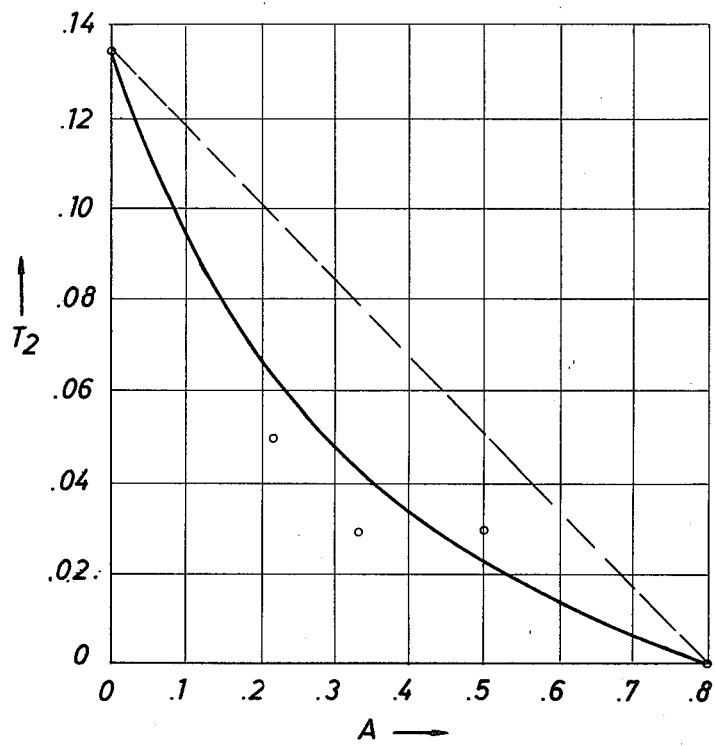
Figure 4:
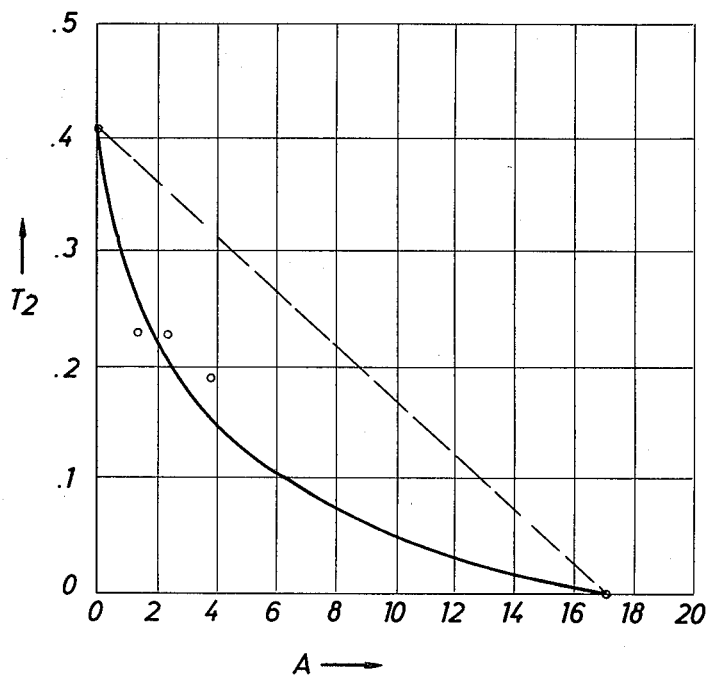

For instance, in FIG. 1, a dotted line is between 0.2 kg/ha of the triazine compound concerned ($T_1$)—indicating the amount of $T_1$ required when used alone to obtain a 90% reduction in the growth of cultivated oat (normally expressed as $GID_{90}$)—and 1.61 kg/ha of the alanine compound concerned (A)—indicating the amount of alanine compound required when used alone to obtain a 90% reduction in the growth of cultivated oat. Since $GID_{90}$ values for mixtures containing specific amounts of the active ingredients in the mixtures when plotted appear to be below the dotted line, a synergistic response has been obtained. Turning to FIG. 2, a similar pattern has been found for the $GID_{50}$ values obtained for barley. It should be noted that, although smaller amounts of the active ingredients are required to obtain the same (undesired) action on barley, the amounts required for such activity are still high enough not to create a problem with respect to selectivity.

EXAMPLE 1

Mixtures of isopropyl N-benzoyl-N-(3-chloro-4-fluorophenyl)-2-aminopropionate as a 20% emulsifiable concentrate (sold commercially as BARNON herbicide) and 2-ethylamino-4-(1-cyano-1-metyl ethylamino)-6-chloro-1,3,5,-triazine were tested as follows.

A number of 7 cm pots of John Innes No. 1 compost were sown with 25–30 seeds of barley, and a number with cultivated oat (Avena sativa). When the plants had reached the 1–1½ leaf stage, a solution of the mixture under test was sprayed, using a logarithmic dilution sprayer, at different doses for each species. Mixtures of fixed dosages of 2-ethylamino-4-(1-cyano-1-methyl ethylamino)-6-chloro-1,3,5-triazine (0.1, 0.03 or 0.01 kg/ha) and a range of dosages of isopropyl-N-(3-chloro-4-fluorophenyl)-2-aminopropionate (0.1–0.4 kg/ha) were used in the experiments.

Assessments were made as fresh shoot weights 22 days after spraying. These values expresses as percentages of the weights for untreated barley and untreated oats were analysed by computor to calculate the growth inhibition dosages to give a 50% reduction for barley and a 90% reduction for oat abbreviated to $GID_{50}$ barley, and $GID_{90}$ oat respectively.

The results are given in FIG. 1 (cultivated oat) and FIG. 2 (barley). The respective $GID_{90}$ figures obtained were 0.61, 0.45 and 0.26 kg/ha. The $GID_{90}$ for BARNON when applied alone is 1.61 kg/ha and for 2-ethylamino-4-(1-cyano-1-methyl-ethylamino)-6-chloro-1,3,5-triazine when applied alone is 0.20 kg/ha. From these results it will be seen that 1.61 kg/ha of the established wild oat herbicide BARNON is required to give 90% reduction in cultivated oat growth when used alone, but when used in admixture with the triazine compound considerably less than that amount is required to give the same growth reduction. It appears from FIG. 1 that when a 10:1 weight ratio of aminopropionate to triazine compound is used only 0.40 kg/ha of the mixture is required to give the same effect whereas in case of an additive response 0.55 kg/ha of the mixture would be required.

EXAMPLE 2

A second series of tests was carried out using mixtures of BARNON and 2-ethylamino-4-(1-cyano-1-methyl ethylamino)-6-chloro-1,3,5-triazine or 2-ethylamino-4-(1-cyano-1-methyl ethylamino)-6-methylthio-1,3,5-triazine. Five mixtures of different proportions of the compounds were sprayed at five dosages each as were the individual compounds.

Assessments were made as fresh weights after 20 days. The barley plants were cut at soil level and the plant weight expressed as a percentage of untreated barley weight. The percentage depression in growth of the oat plants was assessed visually. These figures were analysed by computer to calculate the growth inhibition dosages in kg/ha to give a 50% reduction for barley and oat, respectively.

Figure 5:
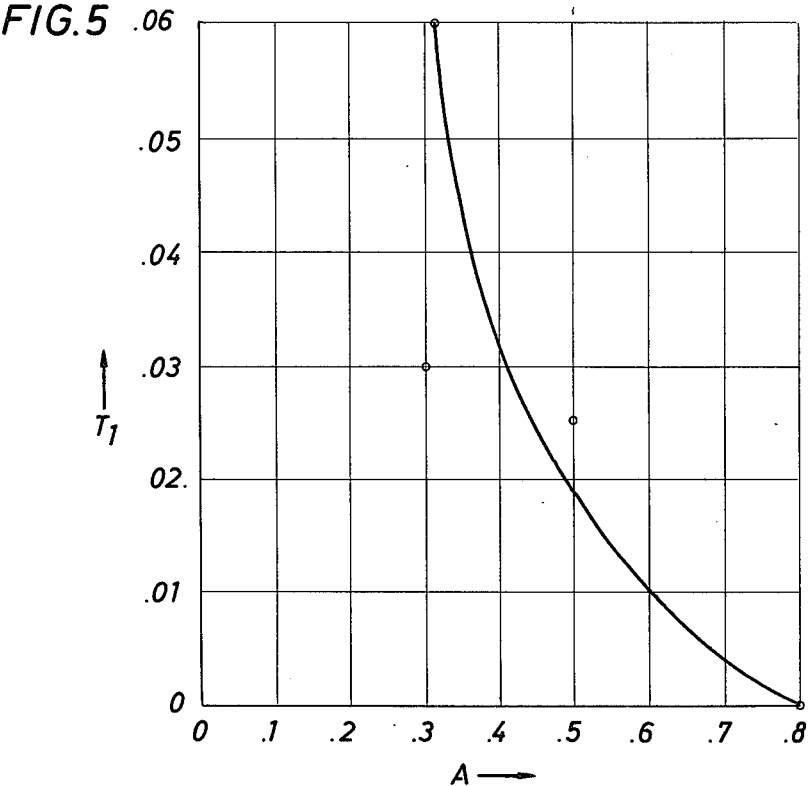
Figure 6:
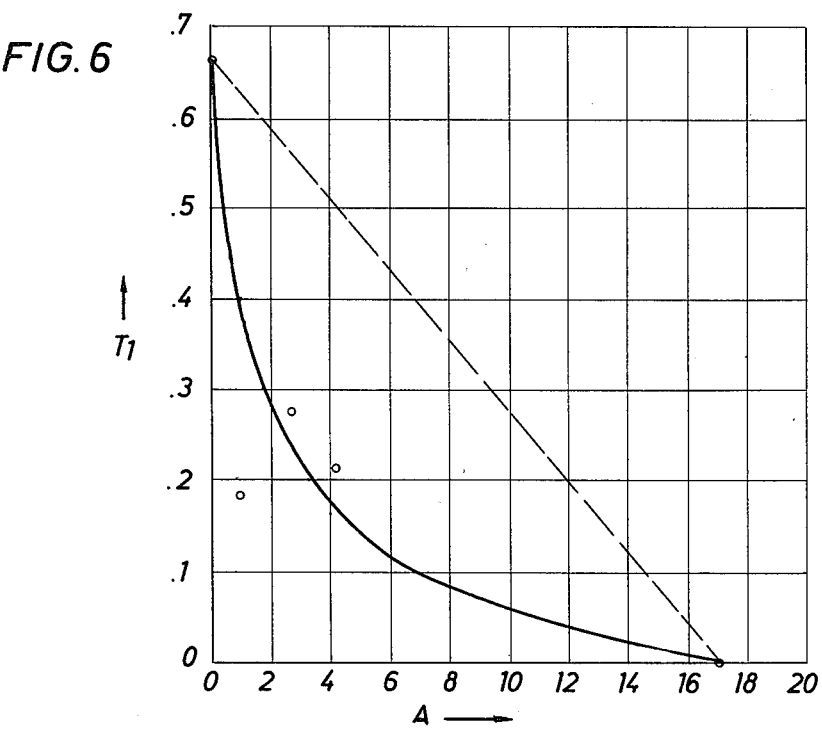

The mixtures were listed using the technique described above. The compounds or mixtures of the two were applied at doses ranging from 8.0 to 0.2 kg/ha on barley and 0.64–0.01 kg/ha on oat. The range of mixtures used and the results obtained are shown in Table 1 and moreover, graphically interpreted in the FIGS. 3–6 wherein $T_1$ stands for the 6-chlorotriazine compound and $T_2$ for the 6-methylthiotriazine compounds. (It should be noted that the 6-chloro-triazine compound used in the amounts as given in FIG. 5 is not active as such against oats).

TABLE 1

Results of mixture trials

| Compound(s) | MIXTURE (proportions by weight) | $GID_{50}$ Barley (kg/ha) | $GID_{50}$ Oat (kg/ha) |
|---|---|---|---|
| B | 1:0 | 17.0 | 0.79 |
| B:T$_1$ | 5:1 | 1.16 | 0.38 |
|  | 10:1 | 3.0 | 0.34 |
|  | 20:1 | 4.4 | 0.53 |
| B:T$_2$ | 5:1 | 1.4 | 0.28 |
|  | 10:1 | 2.5 | 0.37 |
|  | 20:1 | 4.0 | 0.53 |
| T$_1$ | 1:0 | 0.66 | 0.15 |
| T$_2$ | 1:0 | 0.41 | 0.13 |

B = BARNON
T$_1$ = 6-chloro-triazine compound
T$_2$ = 6-methylthio-triazine compound From these results, especially as demonstrated in the FIGS. 3–6, it will be seen that a more than additive effect has been achieved by the mixture.

EXAMPLE 3

A series of tests was carried out using mixtures comprising the wild oat herbicide R-(−)-N-benzoyl-N-(3-chloro-4-fluorophenyl) alanine isopropyl ester ((−)B), 2-ethylamino-4-(1-cyano-1-methyl ethylamino)-6-chloro-1,3,5-triazine (T$_1$) and an ester of (4-chloro-2-methyl phenoxy) propionic acid (CMPP) as indicated in Table 2.

The tests were carried out as described in Example 1. The CMPP esters were applied in amounts of up to 4 kg/ha. Assessments were made as fresh shoot weights 20 days after spraying. The percentage depression of growth of the cultivated oat plants was assessed visually and the mean is given in the right-hand column of Table 2. It will be seen from the data in Table 2 that especially the presence of R-(+)-alkyl esters of (4-chloro-2-methyl phenoxy) propionic acid contributes substantially to the increased overall activity of the −B/T$_1$ mixtures.

TABLE 2

Results of tertiary mixtures

| Compounds in the mixture | Dose Ratio | Phytotoxicity (%) |
|---|---|---|
| (−)B/T$_1$ | 1:0.05 | 85 |
| (−)B/(+) lin CMPP/T$_1$ | 1:3.3:0.05 | 92 |
| (−B/rac lin CMPP/T$_1$ | 1:6.6:0.05 | 79 |
| (−)B/(+)-2 EH CMPP/T$_1$ | 1:3.3:0.05 | 94 |
| (−)B/rac-2 EH CMPP/T$_1$ | 1:6.6:0.05 | 91 | lin = linevol ester
2 EH = ethylhexanol ester
rac = racemate

We claim:
1. A herbicidal composition containing as the herbicide a combination of
(a) 2-ethylamino-4-(1-cyano-1-methylethylamino)-6-chloro-1,3,5-triazine or 2-ethylamino-4-(1-cyano-1-methylethylamino)-6-methylthio-1,3,5-triazine, and
(b) a compound of the formula:

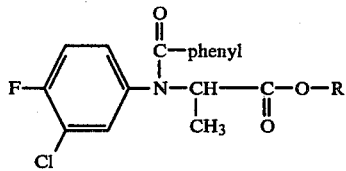

wherein R is methyl, ethyl or isopropyl, the weight ratio of (b) to (a) being within the range of from 1:1 to 50:1.

2. A composition according to claim 1 wherein component (a) is 2-ethylamino-4-(1-cyano-1-methylethylamino)-6-chloro-1,3,5-triazine.

3. A composition according to claim 2 wherein component (b) is in the laevo-rotatory optically-active isomeric form.

4. A composition according to claim 2 wherein R is methyl.

5. A composition according to claim 2 wherein R is ethyl.

6. A composition according to claim 2 wherein R is isopropyl.

* * * * *